United States Patent
Pfrang et al.

(10) Patent No.: US 11,351,299 B2
(45) Date of Patent: Jun. 7, 2022

(54) SYSTEM COMPRISING A PRE-FILLABLE SYRINGE AND A PACKAGE FOR THE PRE-FILLABLE SYRINGE

(71) Applicant: Chiesi Farmaceutici S.p.A., Parma (IT)

(72) Inventors: Jurgen Pfrang, Parma (IT); Andreas Gorshofer, Parma (IT); Marta Lombardini, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 324 days.

(21) Appl. No.: 16/355,343

(22) Filed: Mar. 15, 2019

(65) Prior Publication Data
US 2020/0289741 A1 Sep. 17, 2020

(51) Int. Cl.
| | | |
|---|---|---|
| *A61M 5/00* | (2006.01) | |
| *A61M 5/32* | (2006.01) | |
| *A61M 5/31* | (2006.01) | |
| *A61K 31/485* | (2006.01) | |
| *A61K 9/08* | (2006.01) | |
| *A61J 7/00* | (2006.01) | |
| *B65D 77/20* | (2006.01) | |
| *A61K 9/00* | (2006.01) | |
| *B29L 31/00* | (2006.01) | |
| *B29C 45/16* | (2006.01) | |

(52) U.S. Cl.
CPC .......... *A61M 5/002* (2013.01); *A61J 7/0053* (2013.01); *A61K 9/006* (2013.01); *A61K 9/08* (2013.01); *A61K 31/485* (2013.01); *A61M 5/3137* (2013.01); *A61M 5/3202* (2013.01); *B65D 77/20* (2013.01); *A61M 2205/0216* (2013.01); *A61M 2209/084* (2013.01); *B29C 45/16* (2013.01); *B29L 2031/712* (2013.01)

(58) Field of Classification Search
CPC ... A61M 5/002; A61M 5/3202; A61M 5/3137
USPC .................................................. 206/364, 365
See application file for complete search history.

(56) References Cited

U.S. PATENT DOCUMENTS

| | | | | |
|---|---|---|---|---|
| 4,420,085 | A | * 12/1983 | Wilson .................. | A61M 5/002 206/370 |
| 4,444,310 | A | 4/1984 | Odell | |
| 4,915,233 | A | * 4/1990 | Smith ................... | A61M 5/008 206/366 |
| 5,007,535 | A | * 4/1991 | Meseke ................. | A61M 5/008 206/363 |

(Continued)

FOREIGN PATENT DOCUMENTS

| | | |
|---|---|---|
| EP | 3 095 476 A1 | 11/2016 |
| WO | 97/10014 A1 | 3/1997 |

(Continued)

OTHER PUBLICATIONS

Extended European Search Report dated Aug. 6, 2019, in Patent Application No. 19163093.8, 8 pages.

*Primary Examiner* — Jacob K Ackun
(74) *Attorney, Agent, or Firm* — Oblon, McClelland, Maier & Neustadt, L.L.P.

(57) ABSTRACT

System comprising a pre-fillable syringe with a syringe barrel and a syringe tip and a package suitable and intended for receiving the pre-fillable syringe, wherein the syringe tip is provided with a tip cap, wherein the system comprises a replacement cap for the pre-fillable syringe, wherein the package is suitable and intended for receiving the replacement cap.

17 Claims, 8 Drawing Sheets

(56) References Cited

U.S. PATENT DOCUMENTS

| | | | | | |
|---|---|---|---|---|---|
| 5,566,828 | A | * | 10/1996 | Claes | A61M 5/003 |
| | | | | | 206/570 |
| 8,303,599 | B2 | * | 11/2012 | Hess | A61M 5/1782 |
| | | | | | 606/92 |
| 8,925,723 | B2 | * | 1/2015 | Folchini | A61M 5/002 |
| | | | | | 206/364 |
| 9,668,813 | B2 | * | 6/2017 | Horvath | A61M 5/3202 |
| 10,702,661 | B2 | * | 7/2020 | Perthu | A61M 5/3287 |
| 10,792,431 | B2 | * | 10/2020 | Duinat | A61M 5/3137 |
| 2009/0236259 | A1 | * | 9/2009 | Hicks | A61B 50/30 |
| | | | | | 206/571 |
| 2016/0317761 | A1 | | 11/2016 | Iwase et al. | |
| 2019/0175817 | A1 | | 6/2019 | Ogawa et al. | |

FOREIGN PATENT DOCUMENTS

| | | |
|---|---|---|
| WO | 2014/045336 A1 | 3/2014 |
| WO | 2018/038078 A1 | 3/2018 |

* cited by examiner

SYSTEM COMPRISING A PRE-FILLABLE SYRINGE AND A PACKAGE FOR THE PRE-FILLABLE SYRINGE

TECHNICAL FIELD

The invention relates to a package suitable and intended for receiving a pre-fillable syringe comprising a syringe barrel and a syringe tip, wherein the syringe tip is provided with a tip cap. The invention also relates to a system and the use of the system comprising a pre-fillable syringe with a syringe barrel and a syringe tip and a package suitable and intended for receiving the pre-fillable syringe, wherein the syringe tip is provided with a tip cap. Further, the invention relates to a replacement cap for a pre-fillable syringe.

BACKGROUND

Pre-fillable syringes can be used as a kit together with the medium to be administered or delivered to the user, where the pre-fillable syringes of the kit are filled with the medium.

In particular, nowadays, pre-filled syringes have emerged as one of the fastest-growing choices for unit dose medication. The handling of such syringes is easy because the medium to administer does not need to be transferred to the syringe before the usage. The usage of pre-filled syringes minimizes drug waste and increases product life span.

The administration of drugs to patients, other than by an injection, has become more popular, due to the development of new drugs. Possible ways of administration are, in particular, oral, intranasal, topic, dermal and further external applications. For such applications, pre-filled syringes may be the best way to store, transport and administer the drugs.

Also, for mediums or drugs which are injected in the body, pre-filled syringes are a convenient choice. In particular, modern vaccines react very sensibly to outer influence factors and are therefore securely stored in a pre-filled syringe.

Pre-fillable syringe bodies comprise a syringe barrel, a syringe tip and optionally a finger flange. In some cases, the syringe tip is already provided with a piercing means. A piercing means may be a needle, a canula, or a similar element.

The syringe bodies are produced by a primary packaging producer under clean room conditions. After a sterilization, the syringe bodies are provided with a tip cap and placed in a so-called syringe nest. The tip cap usually is placed on the syringe tip and may also enclose a needle arranged in the syringe tip.

The pre-fillable syringe is then delivered to a pharmaceutical company which either provide a kit together with the medium to administer or, preferably, fills the syringes with the medium.

In the latter case, after the filling process, a plunger or piston is introduced in the syringe barrel, by which the barrel is closed on its proximal side. The filled syringe is then placed in a secondary packaging.

The tip cap can seal the tip and optionally the needle. Usually, the tip caps are at least partially made of an elastic material. Due to the limited space for a syringe in the syringe nest, the tip caps are usually designed as small as possible. Such small sized tip caps may be, however, inconvenient for the user to handle.

In some cases, the user needs to set the dosage before the actual administration of the medium, which may be done at a later point. For this purpose, the tip cap may need to be temporally removed. The reclosing of the syringe with the tip cap may result in an unwanted introduction of a portion of air in the syringe barrel. Such a portion of air may cause irritations to the patient. In cases where the medium in the syringe barrel is a higher-viscosity medium, the enclosed portion of air may be difficult to remove.

SUMMARY OF THE INVENTION

An object of the invention is therefore to provide a pre-fillable syringe, package for receiving a pre-fillable syringe, and a system comprising a pre-fillable syringe and a package that overcomes the above-mentioned disadvantages.

The invention is also directed to the system of the invention, wherein the syringe is pre-filled with a ready-to-use pharmaceutical formulation.

Furthermore, the invention is directed to a kit comprising the system of the invention together with a pharmaceutical formulation in the form of either a ready-to-use aqueous solution or a powder to be reconstituted in a suitable vehicle, and instructions to administer said pharmaceutical formulation.

Figure 1:
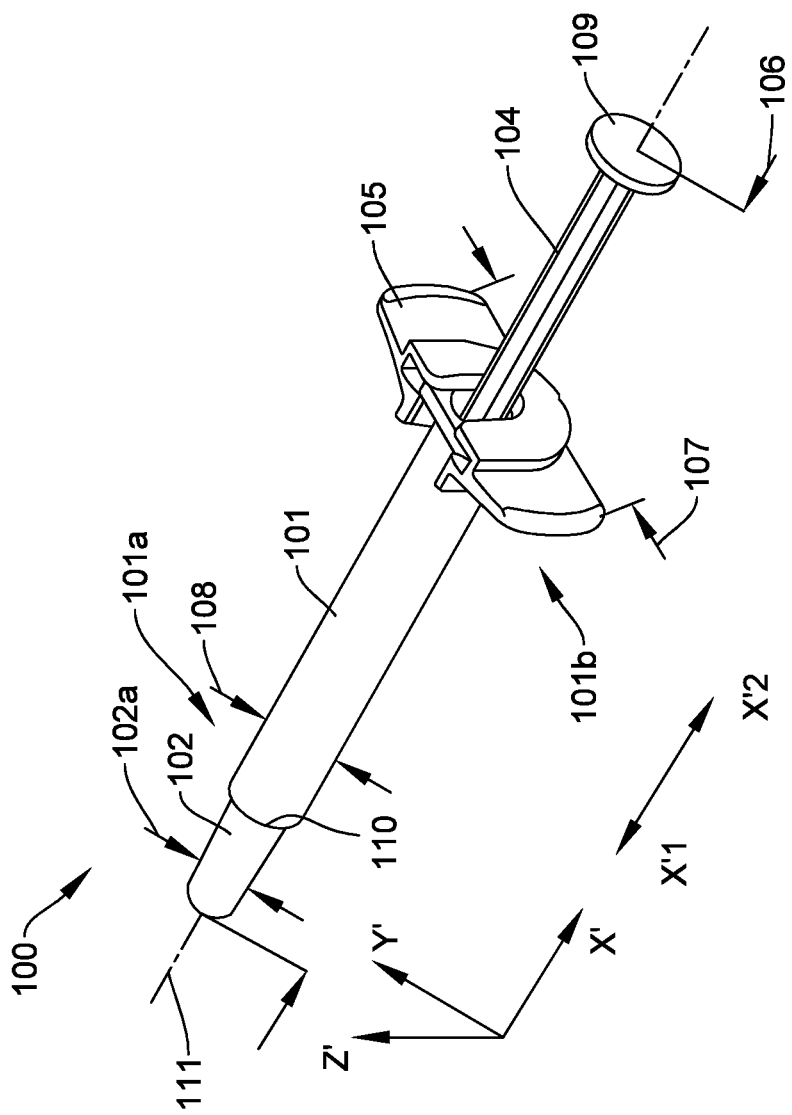
FIG. 1 shows a pre-fillable syringe without a tip cap.

LIST OF REFERENCE NUMERALS 1 package;
2 first receiving element;
3 package body;
4 first cavity of the package body;
5 sidewall of the package body;
6 bottom wall of the package body;
7 second receiving element;
7a first of the second receiving elements;
7b second of the second receiving elements;
8 third receiving element;
8a, 8b walls of the third receiving element;
12 sidewall of the first receiving element;
13 height of the sidewall;
15 closure element;
26 semicircular top section of the second receiving element;
27 base section of the second receiving element;
30 fixture element;
31 flange;
100 pre-fillable syringe;
101 syringe barrel;
101a distal end of the syringe barrel
101b proximal end of the syringe barrel
102 syringe tip;

102a outer diameter of the syringe tip;
103 tip cap;
103a outer diameter of the tip cap;
103b distal end face of the tip cap;
104 rod;
105 finger flange;
106 length of the pre-fillable syringe;
107 width of the finger flange;
108 width of the syringe barrel;
109 finger support;
110 region where the syringe barrel merges into the syringe tip;
111 central axis of the pre-fillable syringe;
112 radius of the syringe barrel;
200 system;
300 replacement cap;
301 inner cap;
302 outer collar;
303 foot portion;
304 opening of the inner cap;
305 ring;
306 struts;
307 center axis of the replacement cap;
308 edge distance;
309 opening of the replacement cap;
309a opening area of the replacement cap;
310 height;
311 bearing area;
312 distal end face of the foot portion;
313 edge of the bearing area;
314 cut portion;
400 support surface;
X longitudinal axis of the package body;
Y horizontal axis of the package body;
Z vertical axis of the package body;
X' longitudinal axis of the pre-fillable syringe;
Y' horizontal axis of the pre-fillable syringe;
Z' vertical axis of the pre-fillable syringe;
X" longitudinal axis of the replacement cap;
Y" horizontal axis of the replacement cap;
Z" vertical axis of the replacement cap;
X'1 distal direction
X'2 proximal direction;
L2 height of the central axis of the syringe above the bottom wall; and
L4 height of the sidewall of the package body.

DETAILED DESCRIPTION

The problem is addressed by a system, comprising a pre-fillable syringe with a syringe barrel and a syringe tip and a package suitable and intended for receiving the pre-fillable syringe, wherein the syringe tip is provided with a tip cap, wherein the system comprises a replacement cap for the pre-fillable syringe, and wherein the package is suitable and intended for receiving the replacement cap.

The system has the advantage that a package, presented to the user, comprises the pre-fillable syringe to use and a suitable replacement cap. The user may retrieve the pre-fillable syringe from the package, remove the tip cap and optionally set the dosage of the pre-fillable syringe. The replacement cap is already available to the user and does not need to be obtained otherwise. Further, the replacement cap does not need to be retrieved from an additional package. For such a retrieval of the replacement cap from the additional package, the user needs to put the possibly already open syringe down. Putting down the pre-fillable syringe could contaminate the syringe tip and implies an unnecessary complicated handling.

On the contrary, the system according to this invention provides the user the pre-fillable syringe and the replacement cap in one package. The replacement cap is therefore always available with the pre-fillable syringe and does not need to be obtained at a time, when the tip cap is possibly already removed. The mounting of the replacement cap may therefore be performed in an uncomplicated manner.

The further use of a replacement cap also has the advantage that the handling of the syringe is easier for the user, since it may be difficult to grasp and remove the comparatively small tip cap.

In the following, the expressions "distal" and "proximal" are understood such that a distal end of a syringe is closer to the application site as the proximal end. The expressions "distal direction" and "proximal directed" are understood analogously.

In the following, the longitudinal axis (X), horizontal axis (Y), and vertical axis (Z) are used in relation to the package body. The longitudinal axis (X'), horizontal axis (Y'), and vertical axis (Z') are used in relation to the pre-fillable syringe. The longitudinal axis (X"), horizontal axis (Y"), and vertical axis (Z") are used in relation to the replacement cap.

According to a preferred embodiment, the package comprises a package body forming a first cavity defined by a sidewall and a bottom wall. Preferably, the pre-fillable syringe is arrangeable in said first cavity. Preferably, the package body extends along a longitudinal axis (X), a horizontal axis (Y) and a vertical axis (Z), which are perpendicular to each other.

According to a preferred embodiment, at least one second receiving element is provided in the first cavity of the package body, in which the syringe barrel is receivable. Preferably two second receiving elements are provided in the first cavity of the package body. Preferably, the at least one second receiving element is arranged on the bottom wall. It is further advantageous that the at least one second receiving element comprises a semicircular top section, arranged on a base section. The semicircular top section extends preferably along the horizontal axis (Y) and the longitudinal axis (X) and is open in the vertical axis (Z). Further, the semicircular top section is suitable and intended for receiving the syringe barrel. The semicircular top section comprises two arms which encompass the syringe barrel at least in part.

According to a further preferred embodiment a distal end of the syringe barrel is supported by a first of the second receiving elements and a proximal end of the syringe barrel is supported by a second of the second receiving elements. It is advantageous that a first of the second receiving elements is located close to or at the region where the syringe barrel merges into the syringe tip. Further, it is preferred that the second of the second receiving elements is located close to the finger flange of the syringe arranged in the package body. Preferably the first and the second of the second receiving elements are separated along the longitudinal axis (X') of the pre-fillable syringe. Thus, in a state where the pre-fillable syringe is arranged in the package body and the syringe barrel is received by the preferably two second receiving elements, a central axis of the pre-fillable syringe extends preferably parallel to the bottom wall of the package body. Advantageously, the central axis extends in a height L2 above the bottom wall. The height L2 is dimensioned such that an easy grasping of the pre-fillable syringe is possible.

According to a further preferred embodiment, at least one third receiving element is provided in the first cavity of the package body, in which a rod of the pre-fillable syringe is receivable. Preferably, the third receiving element comprises two walls extending along the vertical axis (Z), forming a cavity in which the rod is received. Preferably, said walls extend along the longitudinal axis (X). Advantageously, the at least one third receiving element has a bottom wall which is formed semicircularly and connects said walls with each other.

It is further advantageous that a gap between the second of the second receiving elements and the third receiving element is provided. Preferably a finger flange of the pre-fillable syringe projects through said gap such that the finger flange is sandwiched between second of the second receiving elements and the third receiving element. Through this gap, the finger flange of the pre-fillable syringe may preferably project, when the syringe is placed inside the package body. Since the finger flange is preferably sandwiched between the second of the second receiving elements and the third receiving element the pre-fillable syringe is fasted in the package body due to an engagement of the finger flange with the second of the second receiving elements and the third receiving element. The length of said walls is essentially determined by the length of a section of the rod, which projects from the syringe barrel, without the length of the rod in said gap between the second of the second receiving elements and the third receiving element.

According to a preferred embodiment, the pre-fillable syringe further comprises a plunger or a piston connected to a rod projecting out of the syringe barrel. Advantageously, the pre-fillable syringe comprises also a finger flange. The finger flange may be formed on the syringe barrel. It is also conceivable that a separate finger flange element is connected to the syringe barrel, which provides a larger gripping surface. The syringe tip is preferably formed as a cone. Advantageously, the syringe tip has a Luer-Cone. Currently, ISO 80369 governs the Luer standards. The syringe tip may preferably also be equipped with a piercing means, which may be a needle, a canula, or a similar means. The pre-fillable syringe is advantageously provided with a tip cap, which is arranged on the syringe tip. The tip cap may consist at least in part of an elastomeric material. Advantageously, the pre-fillable syringe may consist of glass or plastics.

According to a preferred embodiment, the replacement cap is arranged in the package, such that the replacement cap or an opening of the replacement cap is oriented along a vertical axis (Z) of the package body. Preferably, an opening area of the replacement cap is oriented parallel to the bottom wall of the package body. Such an arrangement allows an easy mounting of the replacement cap on the pre-fillable syringe. The replacement cap does not need to be removed from the package for the mounting process. The pre-fillable syringe may be inserted in the replacement cap, while the replacement cap still remains in the package. Once the replacement cap is mounted on the pre-fillable syringe, the replacement cap is removed together with the pre-fillable syringe from the package. This allows a handling of the syringe with only one hand. Obtaining a separate replacement cap may require a two-hand operation, since the replacement cap needs to be extracted from the separate package and needs to be oriented relative to the pre-fillable syringe, such that a mounting is possible.

According to a preferred embodiment, the replacement cap comprises an inner cap for an engagement with the syringe tip. Advantageously, the replacement cap comprises an outer collar for mounting the replacement cap on the syringe barrel. Further, it is favorable that the replacement cap comprise a foot portion.

The inner cap is preferably arranged on the foot portion of the replacement cap. Advantageously, the inner cap may consist at least partially of an elastomeric material, such that a sealing connection with the syringe tip is possible. The syringe tip may preferably be introduced in the inner cap through an opening of the inner cap.

The outer collar is advantageously formed as a ring which is arranged along a longitudinal axis (X") above the opening of the inner cap. The ring is preferably supported by struts which are arranged at the foot portion and surround the inner cap radially. Preferably, the three struts are placed along the circumference of the ring with an equal distance to each other. The struts project from the ring radially inward and abut at the syringe barrel, when the replacement cap is placed on the pre-fillable syringe.

Preferably, the opening area of the replacement cap is defined by the ring and the opening of the inner cap, which is placed along the longitudinal axis (X") underneath the opening of the ring. The opening of the ring and the opening are advantageously parallel to each other and share the same central axis. Preferably, the opening area of the replacement cap is defined by the ring. The opening area of the replacement cap, which is preferably defined by the ring, and an opening area of the inner cap are preferably oriented parallel to the bottom wall of the package body.

According to a preferred embodiment, a first receiving element is provided in the first cavity of the package body. Preferably, the replacement cap is received in the first receiving element. Advantageously, the foot portion of the replacement cap is received in the first receiving element. The replacement cap is therefore placed upright in the package. Thus, the opening area of the replacement cap is defined by the ring and an opening area of the inner cap are preferably oriented parallel to the bottom wall of the package body.

According to a preferred embodiment, the foot portion is suitable to provide a stable upright positioning of the pre-fillable syringe with the replacement cap on a support surface. Preferably, the foot portion comprises a bearing area which contacts the support surface. Preferably, the bearing area comprises an edge, which surrounds a center axis of the replacement cap at an edge-distance.

For a user, an upright positioning represents a very handy, practical way to place the pre-fillable syringe after removing it from the package. Under an upright positioning, a positioning of the distal end of the pre-fillable syringe on a supporting surface, is understood. Such a positioning bears the advantage that the proximal end is equipped with the finger flange and the rod is easy to grasp. A pre-fillable syringe typically has an extension which is by far larger along the longitudinal axis (X') than along the horizontal axis (Y').

A stable positioning is possible as long as the center of gravity is within an area defined by a tilting edge of the bearing area. The bearing area may stretch over a part of a distal end face of the replacement cap, which constitutes the distal end of the foot portion. It is also conceivable that the bearing area stretches over the entire distal end face. Further, it is conceivable that the bearing area stretches along the edge of the distal end face.

A displacement of the center of gravity in a radial direction may not affect the stability of the standing, as long as the center of gravity is not further radially outwards placed than the tilting edge. Due to the provision of a finger flange at the proximal end of the pre-fillable syringe, the center of gravity is closer to the proximal end of the syringe. This means that a small displacement of the center of gravity can cause the upright standing syringe to topple.

Preferably, the edge-distance between the edge of the bearing area and the center axis is at least twice the radius of the syringe barrel, more preferably, the edge-distance is at least three times the radius of the syringe barrel. Preferably, the edge-distance is at least four times the radius of the syringe barrel. Preferably, the edge-distance is at least five times the radius of the syringe barrel. Due to such an embodiment, the tilting edge is further away from the center axis. Thus, a larger displacement of the center of gravity is possible, before the upright standing syringe topples. Hence, the standing stability is enhanced.

Preferably, the distal end face of the foot portion comprises an edge, surrounding a center axis of the replacement cap at a certain distance. This edge may preferably be parallel to the edge of the bearing area, which is considered as a tilting edge. The edge of the distal end face defines the shape of the foot section, which can be arbitrary. Advantageously, the foot portion has a disc-like shape. Preferably, the foot portion is essentially circular. Alternatively, the foot portion can be rectangular.

After the described equipping of the syringe with a replacement cap, which may be done only one-handed, due to the preferable placement and orientation of the replacement cap in the package, the syringe may be placed standing upright and is easily accessible for the user, when needed.

According to a preferred embodiment, the bearing area and/or the edge surrounding the bearing face is/are coated at least partially with a rubberized material. Such an embodiment bears the advantage that slipping of the foot portion on the supporting surface is inhibited or minimized.

According to a preferred embodiment, the foot portion is designed as a suction cup. A suction cup is a device or object that uses the negative fluid pressure of air to adhere to nonporous surfaces, creating a partial vacuum. The working face of the foot portion is preferably made of elastic, flexible material and has a curved surface. When the center of the foot portion is pressed against a flat supporting surface, the volume of the space between the foot portion and the flat surface is reduced. Thus, the air or water between the foot portion and the surface is to be expelled past the edge of the cup. By this, a lack of pressure develops between the foot portion and the supporting surface. The pressure difference between the atmosphere on the outside of the foot portion and the low-pressure between the foot portion and the supporting surface keeps the foot portion adhered to the surface.

Preferably, the replacement cap is produced by injection molding, preferably by multi-component injection molding.

According to a further preferred embodiment, the sidewall of the package body extends essentially along a vertical axis (Z). By extending essentially, it is meant that the sidewall may have a comparatively small angle ($\alpha$) to the vertical axis (Z). Such an angle could be in a range between 0° to 25°, preferably 0° to 10°, preferably 0° to 5°.

Advantageously, the sidewall of the package body is provided with a flange on its upper end, wherein the flange extends outwards essentially along the longitudinal (X) or the horizontal (Y) axis. Preferably, the flange surrounds the package body.

According to a further preferred embodiment, the package comprises a closure element, which covers the package body at least in part. Preferably, the closure element covers the package body entirely.

According to a further preferred embodiment, the closure element is arranged on the flange, provided on the side walls. The closure element could be a foil or a dimensionally stable element. The closure element could preferably be connected to the flange by a clamping connection, a snap connection, a welded connection or an adhesion bond, or similar connections. Preferably, before the usage, such a connection is torn off, preferably before the usage in order to expose the pre-fillable syringe in the package body.

According to a further preferred embodiment, the closure element is slidably arranged on the package body. Preferably, the closure element is slidable along a slide direction, which is preferably oriented along the longitudinal direction (X). Advantageously, the closure element is provided with a guidance element, which extends along the slide direction, in particular the longitudinal direction (X) on each edge, extending in the direction of the closure element. Preferably, each flange of the two sidewalls extending in the slide direction, in particular the longitudinal direction, is received in a guidance element.

According to a further preferred embodiment, the package may consist of plastic. Preferably, the package is produced in an injection molding process, preferably in a multi-component injection molding process.

The object is also addressed by a package suitable and intended for receiving a pre-fillable syringe comprising a syringe barrel and a syringe tip, wherein the syringe tip is provided with a tip cap, wherein the package is suitable and intended for receiving a replacement cap for the pre-fillable syringe.

The package may comprise the single features or combinations of the features described above for the system. Also, the system may comprise the single features or combinations of the features described for the package. Further, the same advantages may apply for the package as described above for the system.

According to a preferred embodiment, the package comprises a package body, forming a first cavity defined by a sidewall and a bottom wall. Preferably, the pre-fillable syringe is arranged in said first cavity. Advantageously, at least one second receiving element is provided in the first cavity of the package body, in which the syringe barrel is received.

According to a further preferred embodiment a distal end of the syringe barrel may be supported by a first of the second receiving elements and a proximal end of the syringe barrel may be supported by a second of the second receiving elements. It is advantageous that a first of the second receiving elements may be located close to or at the region where the syringe barrel merges into the syringe tip. Further, it is preferred that the second of the second receiving elements may be located close to the finger flange of the syringe arranged in the package body. Preferably the first and the second of the second receiving elements are separated along the longitudinal axis (X') of the pre-fillable syringe. Thus, in a state where the pre-fillable syringe is arranged in the package body and the syringe barrel is received by the preferably two second receiving elements, a central axis of the pre-fillable syringe extends preferably parallel to the bottom wall of the package body. Advantageously, the central axis extends in a height L2 above the bottom wall of the package body.

According to a preferred embodiment, a first receiving element is provided in the first cavity of the package body. Preferably, the replacement cap is received in the first receiving element, such that the replacement cap is oriented along a vertical axis (Z) of the package body and an opening area of the replacement cap is oriented parallel to the bottom wall of the package body. Preferably, the foot portion of the replacement cap is received in the first receiving element. Preferably a bearing area of the replacement cap contacts the bottom wall of the package body.

The object is also addressed by a replacement cap for a pre-fillable syringe, wherein the replacement cap comprises an inner cap for an engagement with the syringe tip, an outer collar for mounting the replacement cap on the syringe barrel and a foot portion replacement cap comprising a foot portion, which is suitable to provide a stable upright positioning of the syringe with the replacement cap on a surface.

The replacement cap may comprise the single features or combinations of the features described above for the system. Also, the system may comprise the single features or combinations of the features described for the replacement cap. Further, the same advantages may apply for the replacement cap as described above for the system.

The inner cap is preferably arranged on the foot portion of the replacement cap. Advantageously, the inner cap may consist at least partially of an elastomeric material, such that a sealing connection with the syringe tip is possible. The syringe tip may preferably be introduced in the inner cap through an opening of the inner cap.

The outer collar is advantageously formed as a ring which is arranged along a vertical axis (Z') above the opening of the inner cap. The ring is preferably supported by struts which are arranged at the foot portion and surround the inner cap radially. Preferably, the three struts are placed along the circumference of the ring with an equal distance to each other. The struts project from the ring radially inward and abut at the syringe barrel, when the replacement cap is placed on the pre-fillable syringe.

Preferably, the opening area of the replacement cap is defined by the ring and the opening of the inner cap, which is placed along the vertical axis (Z) underneath the opening of the ring. The opening of the ring and the opening are advantageously parallel to each other and share the same central axis. Preferably, the opening area of the replacement cap is defined by the ring. The opening area of the replacement cap, which is defined by the ring, and an opening area of the inner cap are preferably oriented parallel to the bottom wall of the package body.

According to a preferred embodiment, the foot portion is suitable to provide a stable upright positioning of the pre-fillable syringe with the replacement cap on a surface. For a user, an up-right positioning represents a very handy, practical way to place the syringe. An upright positioning can mean a positioning of the distal end on a supporting surface, such that the proximal end, equipped with the finger flange and the rod, is easy to grasp.

Preferably, the foot portion comprises an edge, surrounding a center axis of the replacement cap. This edge may be considered as the above-mentioned tilting edge. The edge defines the shape of the foot section, which can be arbitrary. Preferably, the foot portion has a disc-like shape. Advantageously, the foot portion has a disc-like shape. Preferably, the foot portion has an essentially circular base area. Preferably, the foot portion has a base area which is essentially rectangular. Preferably, the distance between the edge and the center axis is at least twice the radius of the syringe barrel, more preferably the distance between the edge and the center axis is at least three times the radius of the syringe barrel. Preferably, the distance between the edge and the center axis is at least four times the radius of the syringe barrel. Preferably, the distance between the edge and the center axis is at least five times the radius of the syringe barrel. Due to such an embodiment, the tilting edge is further away from the center axis. Thus, a larger displacement of the center of gravity is possible before the up-right standing syringe topples. Hence, the standing stability is enhanced.

After the described equipping of the syringe with a replacement cap, which may be done only one-handed, due to the preferable placement and orientation of the replacement cap in the package, the syringe may be placed upright standing and is easily accessible for the user, when needed.

According to a preferred embodiment, the bearing area and/or the edge surrounding the bearing face is/are coated at least partially with a rubberized material. Such an embodiment bears the advantage that slipping of the foot portion on the supporting surface is inhibited.

According to a preferred embodiment, the foot portion is designed as a suction cup. A suction cup is a device or object that uses the negative fluid pressure of air to adhere to nonporous surfaces, creating a partial vacuum. The working face of the foot portion is preferably made of elastic, flexible material and has a curved surface. When the center of the foot portion is pressed against a flat supporting surface, the volume of the space between the foot portion and the flat surface is reduced. Thus, the air or water between the foot portion and the sur-face is to be expelled past the edge of the cup. By this, a lack of pressure develops between the foot portion and the supporting surface. The pressure difference between the atmosphere on the outside of the foot portion and the low-pressure between the foot portion and the supporting surface keeps the foot portion adhered to the surface.

Preferably, the replacement cap may consist of a plastics material. Preferably the replacement cap is produced by injection molding, preferably by multi-component injection molding.

The object is also addressed by a use of a system according to any of the above-mentioned embodiments, comprising the following steps,
 a) retrieving the pre-fillable syringe from the package;
 b) removing the tip cap from the syringe tip;
 c) placing the syringe tip in the replacement cap, which is arranged in the package; and
 d) retrieving the pre-fillable syringe with the replacement cap attached to it from the package.

The use of the system may comprise the single features or combinations of the features described above for the system or package. Also, the system or the package may comprise the single features or combinations of the features described above for the use. Further, the same advantages may apply for the use of the system as described above for the system or the package.

According to a preferred embodiment, the use comprises the step to set the dosage of the pre-fillable syringe.

According to a preferred embodiment, the usage may also comprise the step of removing the closure element.

According to a preferred embodiment, the syringe may be placed in an upright position on a support surface after the retrieval of the syringe equipped with the replacement cap of the package. Preferably, a foot portion of the replacement cap is suitable to provide a stable upright positioning of the pre-fillable syringe with the replacement cap on the support surface. Preferably, a bearing area of a foot portion of the replacement cap contacts the support surface.

In the following, the longitudinal axis (X), horizontal axis (Y), and vertical axis (Z) are used in relation to the package body (3). The longitudinal axis (X'), horizontal axis (Y'), and vertical axis (Z') are used in relation to the pre-fillable syringe (100). The longitudinal axis (X"), the horizontal axis (Y"), and the vertical axis (Z") are used in relation to the replacement cap (300).

In FIGS. 1, 2a, 3, 4, and 5a, a pre-fillable syringe is displayed. A pre-fillable syringe (100) comprises a syringe barrel (101) and a syringe tip (102). The syringe barrel (101) is cylindrically shaped and open at its proximal end. At its distal end, the syringe barrel (101) merges along the distal direction (X'1) into the syringe tip (102). The syringe tip (102) may have the form of a cone. Advantageously, the syringe tip (102) is a Luer-cone. It is also conceivable that a piercing means, in particular a needle, a canula, or a similar means, is arranged in the syringe tip (102). In the syringe barrel (101), the medium to administer is stored. On its proximal end, the syringe barrel (101) is closed with a plunger or a piston (not visible in the figures), which is movable in the syringe barrel (101). The plunger or the piston are attached to a rod (104), which projects in the proximal direction (X'2) from the syringe barrel (101). On the proximal end of the rod (104), a finger support (109) is arranged. Further, the syringe barrel (101) is provided with a finger flange (105). In the present case, the finger flange (105) is a clip-on-finger flange. which may be clipped on a finger flange on the syringe barrel (101). Such clip-on-finger flanges bear the advantage of a larger area to grasp for the user.

The pre-fillable syringe (100) is provided with a tip cap (103) which is arranged on the syringe tip (102). The tip cap (103) may consist at least in part of an elastomeric material.

Figure 2A:
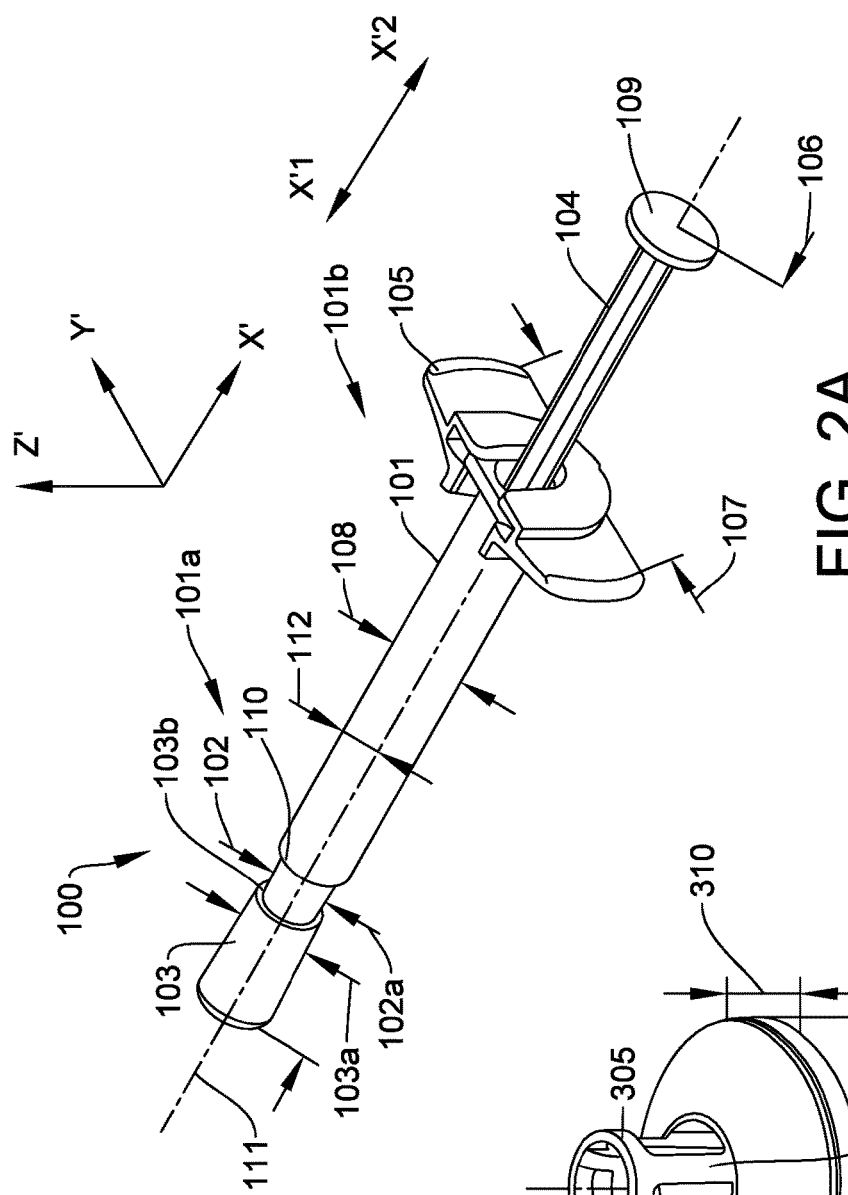
FIG. 2a shows a pre-fillable syringe with a tip cap.
Figure 2B:
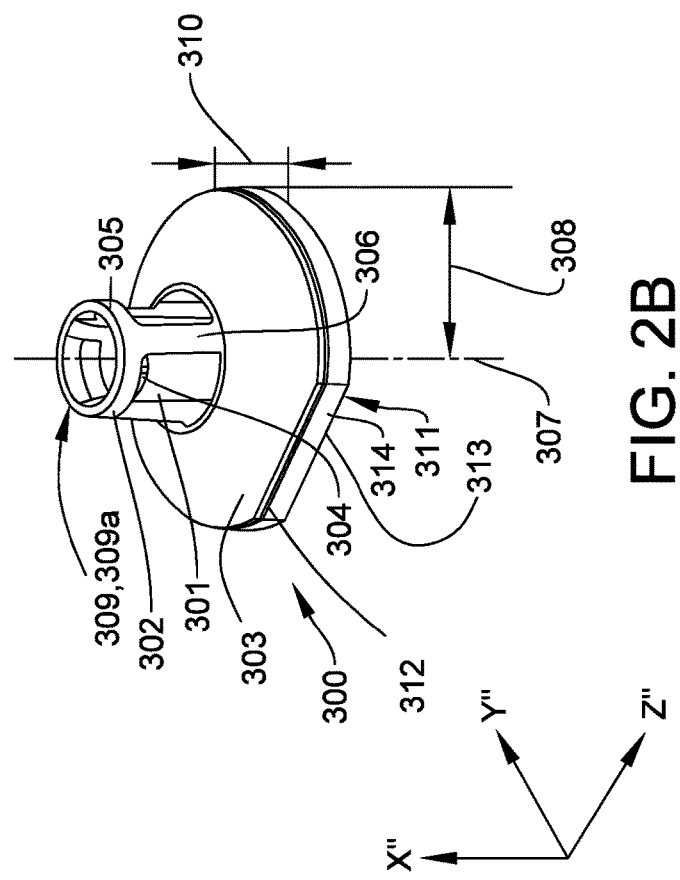
FIG. 2b shows a replacement cap.
Figure 3:
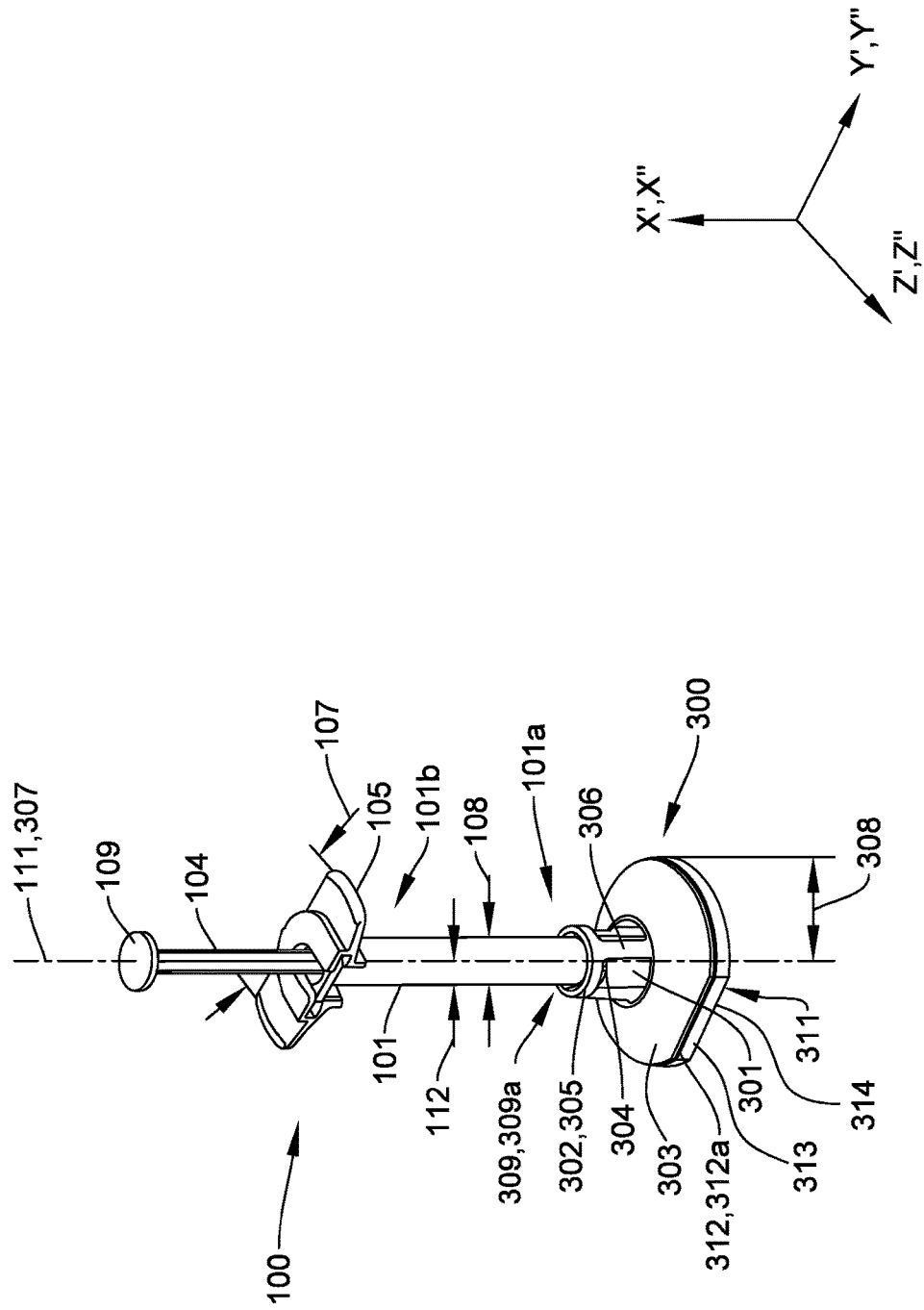
FIG. 3 shows a pre-fillable syringe with a replacement cap.
Figure 4:
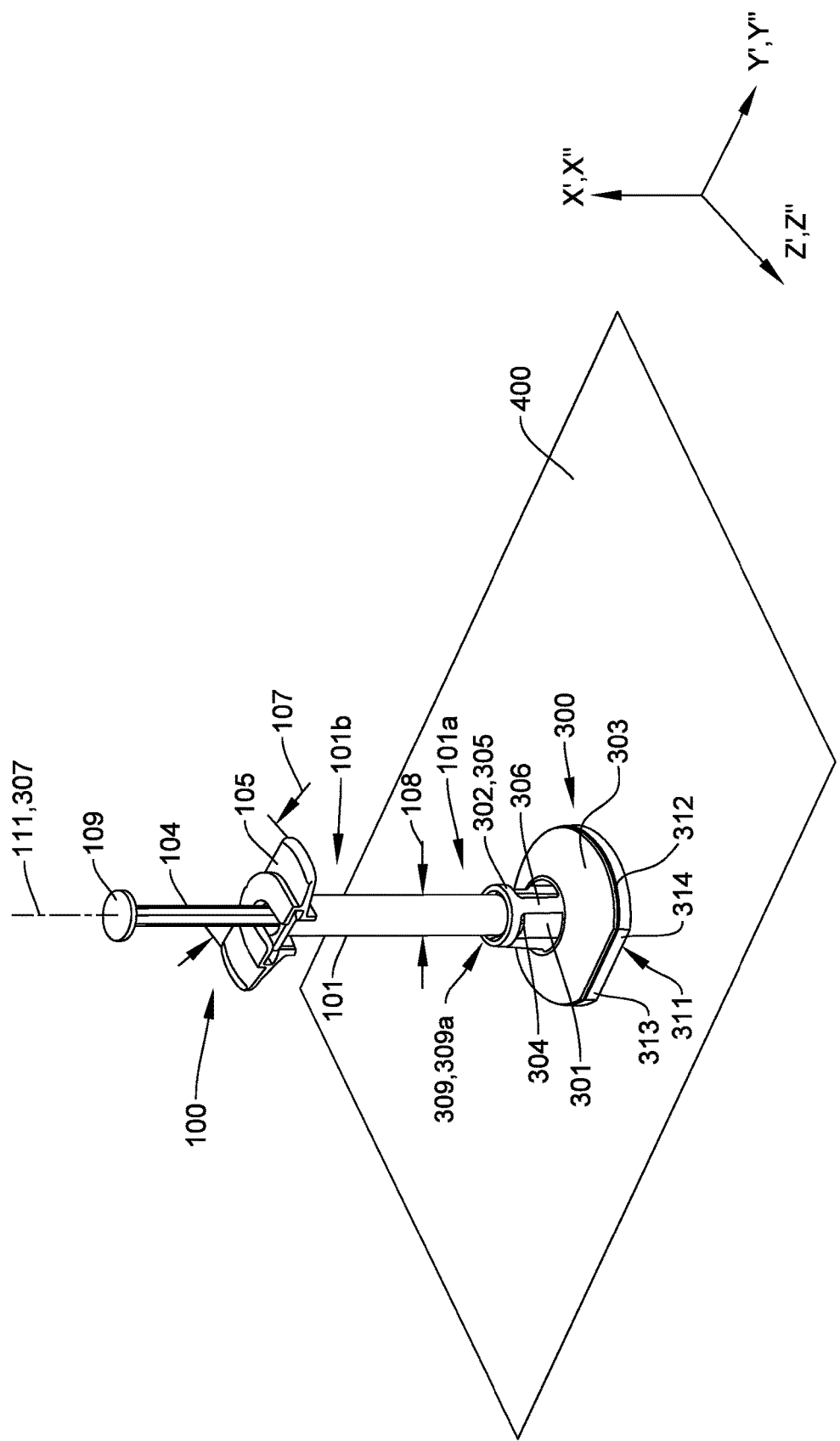
FIG. 4 shows a pre-fillable syringe with a replacement cap on a support surface.
Figure 5A:
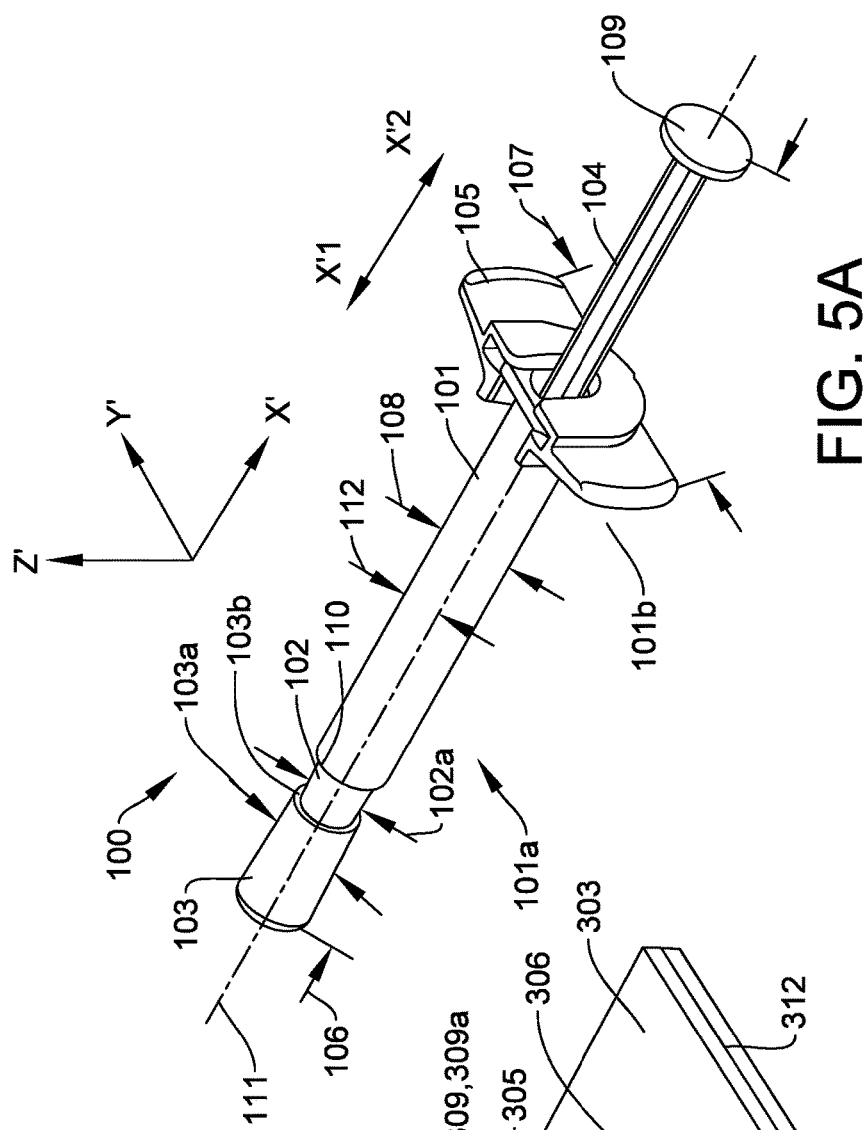
FIG. 5a shows a pre-fillable syringe with a tip cap.
Figure 5B:
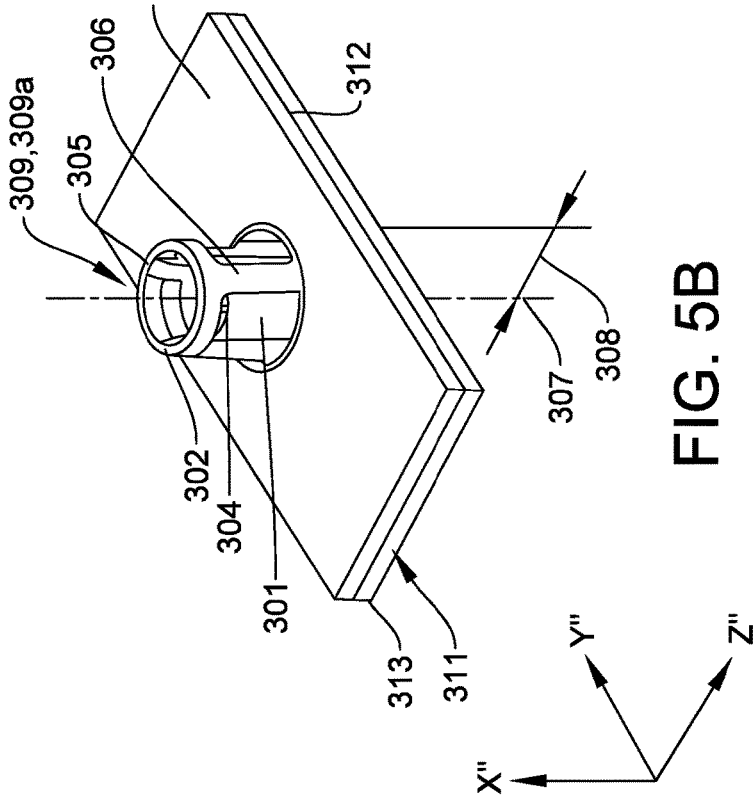
FIG. 5b shows a replacement cap.
Figure 7:
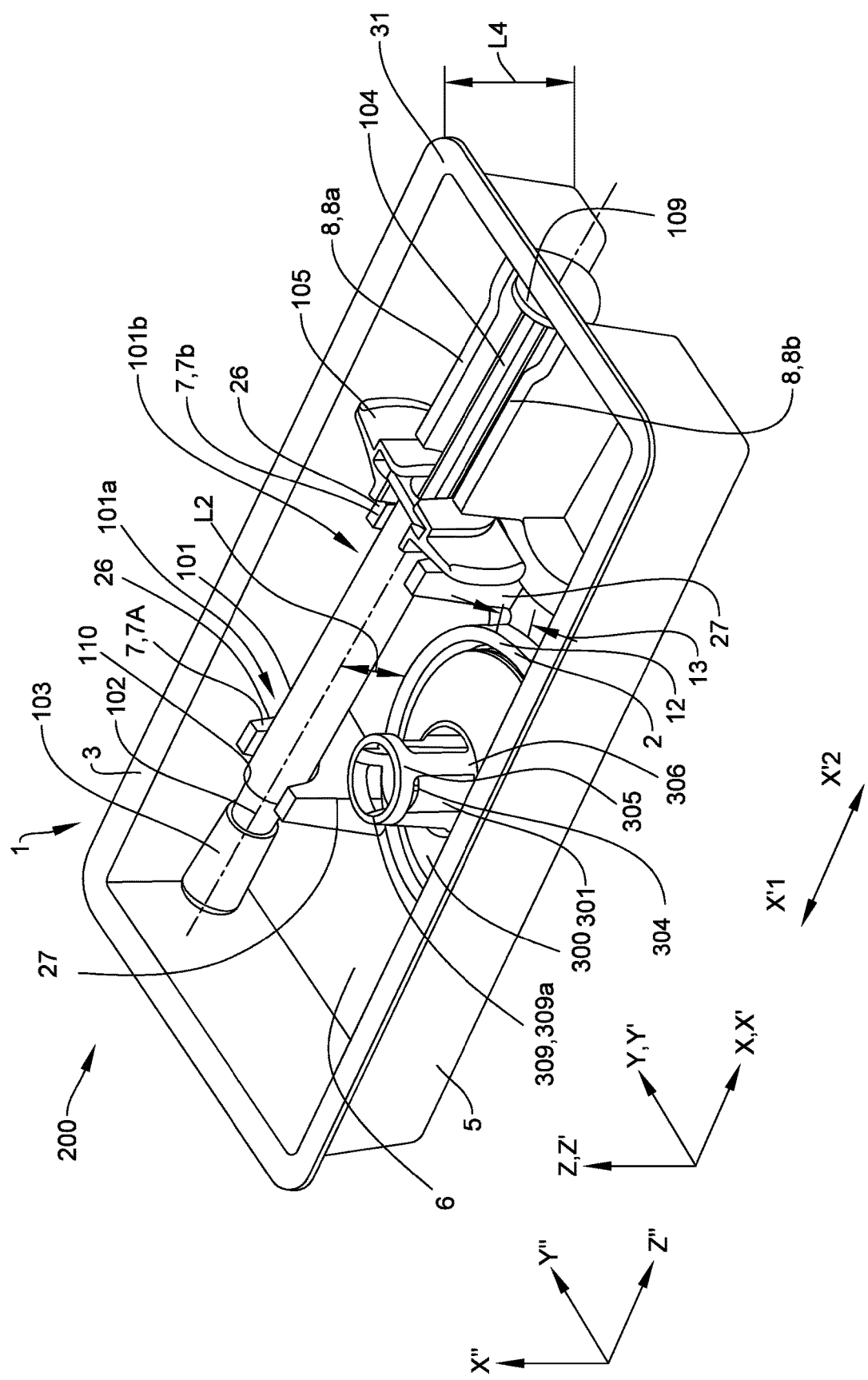
FIG. 7 shows a package body according to one embodiment with a pre-fillable syringe and a replacement cap.
Figure 8:
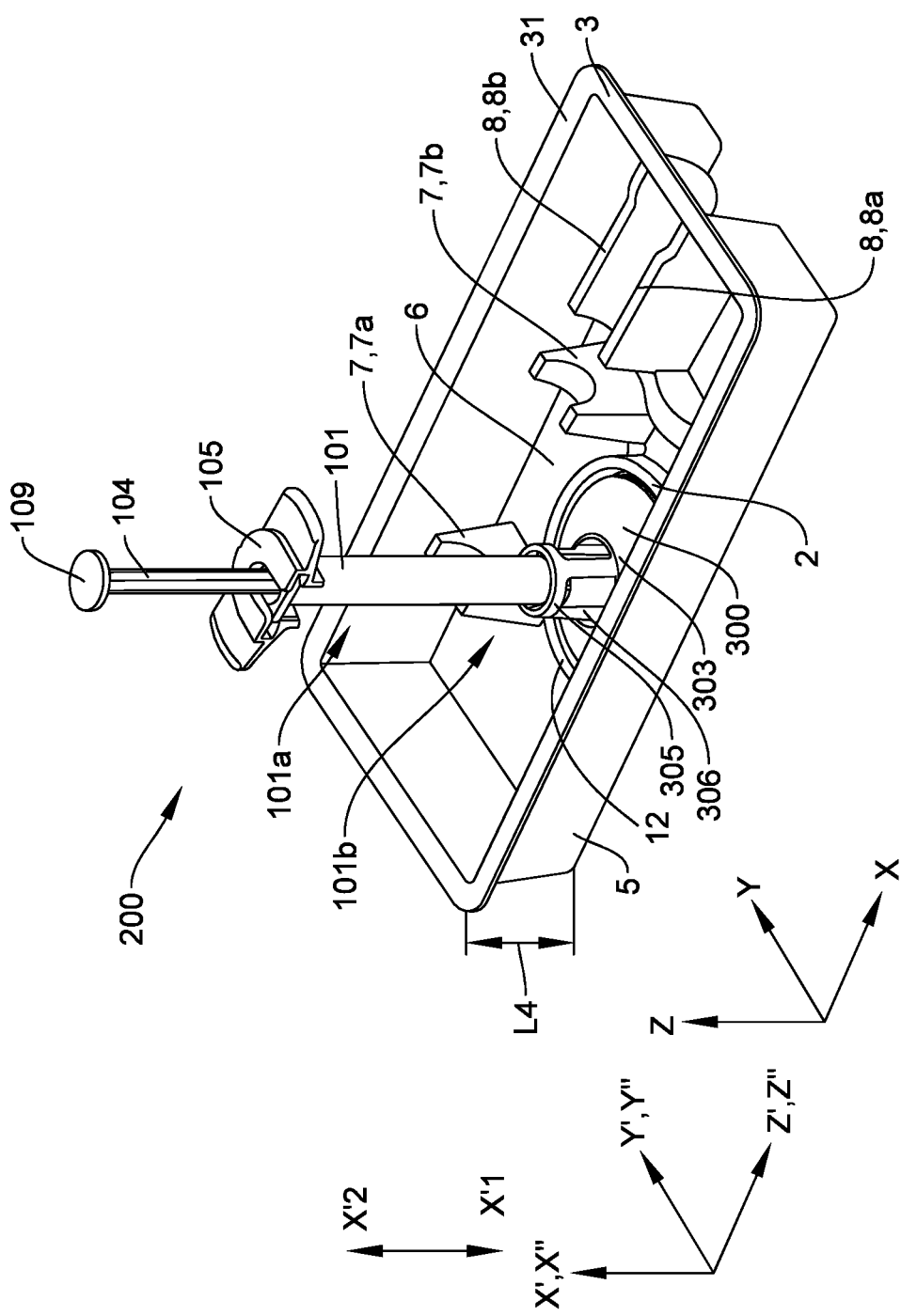
FIG. 8 shows a package body according to one embodiment with a pre-fillable syringe placed in a replacement cap.

In FIGS. 2b and 5b, a replacement cap (300) is depicted. In FIGS. 3, 4 and 8, a pre-fillable syringe (100) is depicted, which is equipped with a replacement cap (300). In FIGS. 7, 8 and 10, a package (1) is shown, in which a replacement cap (300) is arranged.

The replacement cap (300) comprises an inner cap (301) for an engagement with the syringe tip (102). The inner cap (301) is arranged on a foot portion (303) of the replacement cap. Preferably, the inner cap (301) may consist at least partially of an elastomeric material, such that a sealing connection to the syringe tip (102) is possible. The syringe tip (102) may be introduced in the inner cap (301) through the opening (304) of the inner cap (301).

Further, the replacement cap (300) comprises an outer collar (302) for mounting the replacement cap (300) and a foot portion (303).

The outer collar (300) comprises a ring (305) which is arranged along the longitudinal axis (X") above the opening (304) of the inner cap (301). The ring (305) is supported by struts (306). Preferably, three struts (306) are placed along the circumference of the ring (305) with an equal radial distance to each other. The struts (306) are arranged at the foot portion (303) and surround the inner cap (301) radially. Further, the struts (306) project from the ring (305) radially inward and abut at the syringe barrel (101), when the replacement cap (300) is placed on the pre-fillable syringe (100).

The replacement cap (300) comprises an opening (309) and an opening area (309a), which is defined by the ring (305). The opening (304) of the inner cap (301) is placed along the longitudinal axis (X") underneath the ring opening (309). Thus, the opening area (309a) is oriented parallel to an opening area of the opening (304) of the inner cap (301). The pre-fillable syringe (100) is introduced first through the opening (309) and then into the opening (304) of the inner cap (301). The opening (309) and the opening (304) share the same center axis (307). In FIGS. 7 and 8, a package (1) is shown, in which a replacement cap (300) is arranged. The opening area (309a) is then oriented parallel to the bottom wall (6) of the package body (3).

The foot portion (303) is suitable to provide a stable upright positioning of the pre-fillable syringe (100) on a support surface (400). This is depicted in FIG. 4. Under an upright positioning a positioning of the distal end of the pre-fillable syringe (100) on a support surface (400) is understood, such that the proximal end of the pre-fillable syringe (100), which is equipped with the finger flange (105) and the rod (104), is easy to grasp. The foot portion (303) comprises a bearing area (311), which contacts the supporting surface (400). The bearing area (311) may stretch over a part of a distal end face (312) of the replacement cap (300), which constitutes the distal end of the foot portion. It is also conceivable that the bearing area (311) stretches of the entire distal end face (312). Further, it is conceivable that the bearing area (311) stretches along the edge of the distal end face (312).

The pre-fillable syringe (100) has an extension which is by far larger along the longitudinal axis (X') than along the horizontal axis (Y'). A stable positioning is possible as long as the center of gravity is within an area defined by an edge of the bearing area (311). A displacement of the center of gravity in a radial direction (along the horizontal axis (Y') or the vertical axis (Z')) may not affect the stability of the standing as long as the center of gravity is not further radially outwards placed than the tilting edge. Due to the provision of a finger flange (105) at the proximal end of the pre-fillable syringe (100), the center of gravity is closer to the proximal end of the pre-fillable syringe (100). This means that a small displacement of the center of gravity causes the upright standing syringe to topple.

The bearing area (311) comprises an edge (313) which surrounds a center axis (307) of the replacement cap (300) at an edge-distance (308). The edge-distance (308) is at least twice the radius (112) of the syringe barrel (101), more preferably the edge-distance (308) is at least three times the radius (112) of the syringe barrel (101). Preferably, the edge-distance (308) is at least four times the radius (112) of the syringe barrel (101). Preferably, the edge-distance (308) is at least five times the radius (112) of the syringe barrel (101). Due to such an embodiment, the tilting edge is further away from the center axis. It is therefore a larger displacement necessary to tip the pre-fillable syringe (100) over.

The distal end face (312) of the foot portion (303) comprises an edge. The edge of the distal end face (312) and the edge (313) of the bearing area (311) are parallel to each other and adjacent.

In the FIGS. 2b, 3, 4, 7, and 8, the replacement cap (300) has a disc-like shape which is essentially circular, except for a cut portion (314). Said edge distance (308) is therefore essentially the radius of the disc-like shaped foot portion (313). The cut portion (314) extends along a secant line, meaning a line that intersects the circular replacement cap on two points of the diameter, wherein the secant does not run through the center of the circular replacement cap. The cut portion (314) is adjacent to a sidewall (5) extending along the longitudinal axis (X).

The foot portion (303) according an embodiment of FIG. 5b is rectangular. The edge-distance (308) would therefore be the distance to the edge closest to the center axis (307).

The foot portion (303) is, due to its dimension, also a suitable grip portion for the user to grasp the replacement cap (300). The foot portion (303) may also be designed as a suction cup, which is a device or object that uses the negative fluid pressure of air to adhere to nonporous surfaces, creating a partial vacuum.

Figure 6:
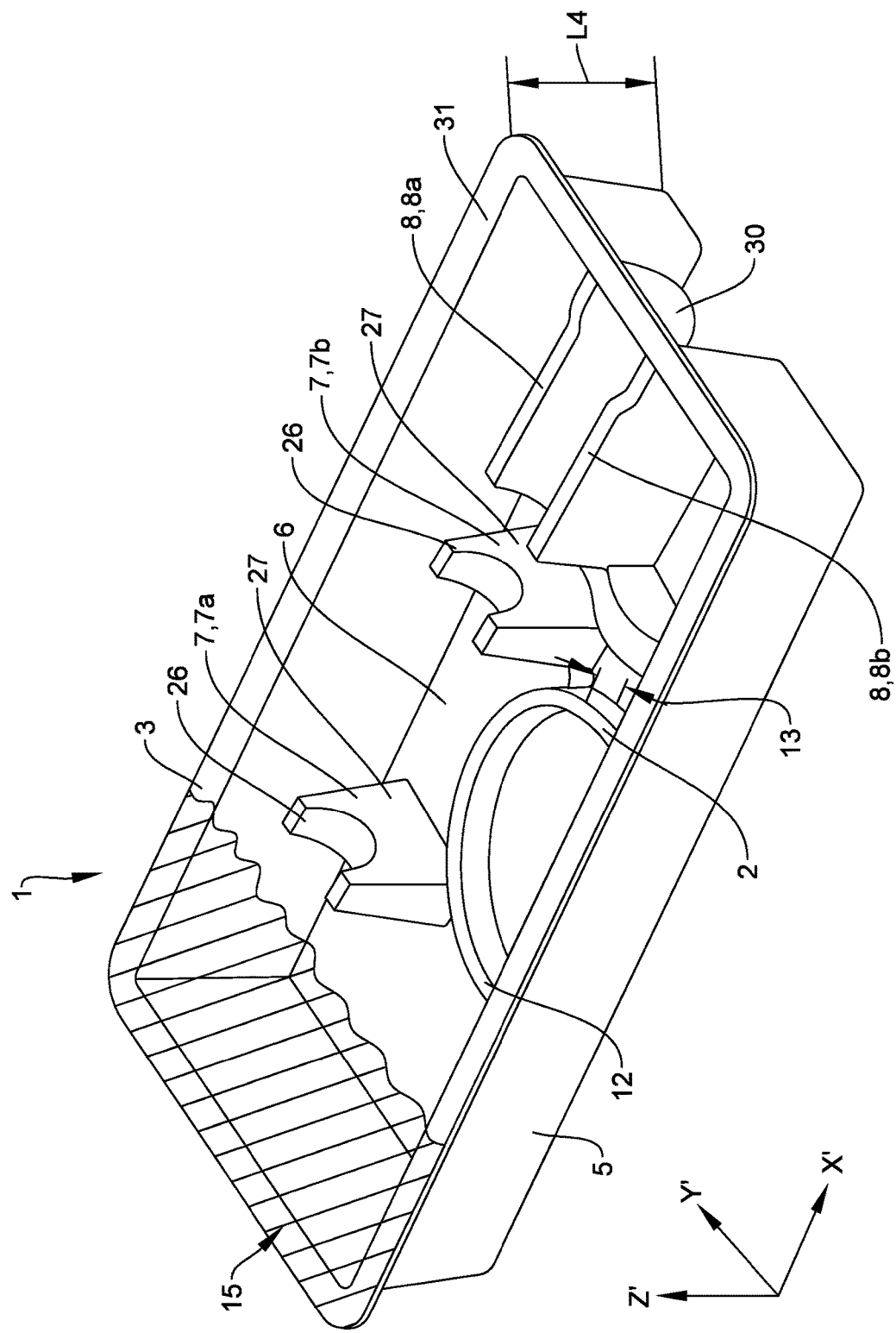
FIG. 6 shows a package body according to one embodiment without a pre-fillable syringe.

In the FIGS. 6 to 8, a package (1) and/or a system (200) are depicted.

The system (200) comprises a pre-fillable syringe (100) with a syringe barrel (101) and a syringe tip (102) and a package (1) suitable and intended for receiving the pre-fillable syringe (100), wherein the syringe tip (102) is provided with a tip cap (103), wherein the system (200) comprises a replacement cap (300) for the pre-fillable syringe (100), and wherein the package (1) is suitable and intended for receiving the replacement cap (300).

The package (1) suitable and intended for receiving a pre-fillable syringe (100) comprises a syringe barrel (101) and a syringe tip (102), wherein the syringe tip (102) is provided with a tip cap (103), wherein the package (1) is suitable and intended for receiving a replacement cap (300) for the pre-fillable syringe (100).

The package (1) comprises a package body (3), forming a first cavity (4), defined by a sidewall (5) and a bottom wall (6), wherein the pre-fillable syringe (100) is arrangeable or arranged in said first cavity (4). The package body (3) extends along a longitudinal axis (X), a horizontal axis (Y), and a vertical axis (Z), which are perpendicular to each other. Further, the package body (3) has a rectangular shape.

At least one second receiving element (7, 7a, 7b) is provided in the first cavity (4) of the package body (3), in which the syringe barrel (101) is receivable. The embodiments shown in the figures have two second receiving elements (7, 7a, 7b), which are arranged at the bottom wall (6) of the package body (3).

The first (7a) of the second receiving elements (7) comprise a semicircular top section (26) arranged on a base section (27). The semicircular top section (26) is dimensioned to receive the syringe barrel (101). According the embodiments in FIGS. 6 to 8, the second (7b) of the second receiving elements (7) also comprises a semicircular top section (26) arranged on a base section (27).

A distal end (101a) of the syringe barrel (101) is supported by a first (7a) of the second receiving elements (7), and a proximal end (101b) of the syringe barrel (101) is supported by a second (7b) of the second receiving elements (7).

In case the pre-fillable syringe (100) is arranged in the package (1), the first (7a) of the second receiving elements (7) is located close to or at the region (110), where the syringe barrel (101) merges into the syringe tip (102). Further, the second (7b) of the second receiving elements (7) is located close to the finger flange (105) of the pre-fillable syringe (100) arranged in the package body (3).

The first cavity (4) of the package body (3) is provided with a third receiving element (8), in which the rod (104) of the pre-fillable syringe (100) is receivable or received. The third receiving element (8) comprises two walls (8a, 8b) extending along the vertical axis (Z), forming a cavity in which the rod (105) is receivable or received. Further, the third receiving element (8) has a bottom wall, formed semicircularly, and connecting the walls (8a, 8b). The third receiving element (8) ends at its proximal end in a fixture element (30), in which the finger support (109) of the rod (104) is received.

Between the second of the second receiving elements (7, 7b) and the third receiving element (8), a gap (29) is formed. Through this gap (29), the finger flange (105) of the pre-fillable syringe (100) may project, when the pre-fillable syringe (100) is placed inside the package body (3). Thus, the finger flange (105) is sandwiched between the second (7b) of the second receiving elements (7) and the third receiving element (8), such that the pre-fillable syringe (100) is fastened in the package body (3).

The third receiving element (8) stretches, after the gap (29), essentially along the length of the section of the rod (104) projecting from the syringe barrel (101).

When the pre-fillable syringe (100) is placed in the package body (3), it is supported by the first (7a) of the second receiving elements (7), preferably by the second (7b) of the second receiving elements (7), and preferably by the third receiving element (8), in particular by the fixture element (30). Thus, in a state where the pre-fillable syringe (100) is in the package body (3), a central axis (111) of the pre-fillable syringe (100) extends parallel to the bottom wall (6) of the package body (3). The central axis (111) extends in a height L2 above the bottom wall (6) of the package body (3). The height L2 allows an easy grasping of the pre-fillable syringe (100).

The replacement cap (300) is arranged in the package (1), such that an opening (309) of the replacement cap (300) is oriented along a vertical axis (Z) of the package body (3). An opening area (309a) of the replacement cap (300) is oriented parallel to the bottom wall (6) of the package body (3). Preferably the center axis (307) of the replacement cap (300) is parallel to the height extension of the sidewalls (5) of the package body (3).

The side wall(s) (5) of the package body (3) surround the package body (3) along the longitudinal axis (X) and the horizontal axis (Y). The sidewall(s) (5) extend(s) along the vertical axis (Z) with a height L4. The height L4 is at least the height L2 plus the radius (112) of the syringe barrel (101). The upper (along the vertical axis (Z)) end of the side wall(s) (5) is provided with a flange (31). The flange (31) extends outwards and surrounds the package body (3) along the longitudinal axis (X) and the horizontal axis (Y), preferably without any gap.

On the flange (31), a closure element (15) may be arranged. Preferably the closure element is connected with a suitable connection to the flange (31). The closure element (15) is shown only partly in FIG. 6 and may be a foil or a slidable stable element.

According to the embodiment of FIGS. 6 to 8, the first cavity (4) of the package body (3) is provided with a first receiving element (2), in which the replacement cap (300) is received. In particular, wherein the foot portion (303) of the replacement cap (300) is received in the first receiving element (2). The first receiving element (2) therefore essentially is the shape of the outer perimeter of the foot portion (303). In case of the FIGS. 6 to 8 this shape would be essentially circular with a cut portion extending along a secant.

The first receiving element (2) comprises a sidewall (12), which is arranged on the bottom wall (6) of the package body (3). This sidewall (12) and the sidewall (5) of the package body (3) define a cavity, which complies with the shape of the foot portion (303) of the replacement cap (300). In the present case of FIGS. 6 to 8, this cavity and the foot portion (303) of the replacement cap (300) are shaped essentially circularly. The bearing surface (311) of the replacement cap (300) sits therefore on the bottom wall (6) of the package body (3), such that the replacement cap (300) is arranged in the package (1), such that an opening (309) of the replacement cap (300) is oriented along a vertical axis (Z) of the package body (3). An opening area (309a) of the replacement cap (300) is oriented parallel to the bottom wall (6) of the package body (3).

The height (13) of the sidewall (12) along the vertical axis (Z) is essentially the height (310) of the replacement cap (300) at its outer edge.

In the FIGS. 1 to 8, also a use of the system (200) is displayed. The use comprises preferably removing the closure element from the package body (3). The pre-fillable syringe (100) is then retrieved from the package (1). Then, the tip cap (103) is removed. Optionally, the dosage of the pre-fillable syringe is set. Then, the replacement cap (300) is mounted on the pre-fillable syringe (100). For this, the syringe tip (102) is placed in the replacement cap (300) which is arranged in the package (1). The syringe tip (102) is let through the opening (309) of the replacement cap (300) and the opening (304) of the inner cap (301). Eventually, the inner cap (301) is attached to the syringe tip (102) and the ring (305) or the struts (306) abut on the syringe barrel (101). During the mounting, the replacement cap (300) is still inside the package (1). Since the opening (309) of the replacement cap (300) is oriented along the vertical axis (Z) of the package body (3), the syringe tip (102) may easily be introduced into the replacement cap (300). The handling of the syringe (100) is therefore possible using only one hand. It is not necessary to put the pre-fillable syringe (100) down to obtain or align the replacement cap (300) relative to the pre-fillable syringe (100). The pre-fillable syringe (100) with the replacement cap (300) attached to it may then be retrieved from the package (1).

The pre-fillable syringe (100) may preferably be placed in an upright position on a support surface (400). Preferably, a foot portion (303) of the replacement cap (300) is suitable to provide a stable upright positioning of the pre-fillable syringe (100) with the replacement cap (300) on the support surface (400), wherein a bearing area (311) of a foot portion (303) of the replacement cap (300) contacts the support surface (400).

Such a system (200) has the advantage that a package (1) is presented to the user which comprises the pre-fillable syringe (100) to use and a suitable replacement cap (300). The replacement cap (300) is already available to the user and does not need to be obtained otherwise. Further, the replacement cap (300) does not need to be retrieved from an additional package.

The invention is also directed to the system herein disclosed, wherein the syringe is pre-filled with a ready-to-use pharmaceutical formulation.

Advantageously, the pharmaceutical formulation is in form of solution or emulsion and comprises one or more active ingredients suitable for oral, intramuscular or intravenous administration.

More advantageously, the formulation is an aqueous solution or a hydroalcoholic solution.

Preferably, the pharmaceutical formulation is an aqueous solution or a hydroalcoholic solution comprising buprenorphine, for an efficacious treatment by sublingual and/or buccal administration of patients affected by opiate withdrawal syndrome (OWS), more preferably neonates affected by neonatal OWS.

More preferably, the buprenorphine formulation in form of aqueous solution comprises:
i) from 0.005 to 0.02% w/v of buprenorphine or a pharmaceutically acceptable salt thereof as the sole active ingredient;
ii) from 0.5% to 10% w/v of a thickening agent; and
iii) a buffering agent in an amount to provide a pH of 5.0-7.0.

Buprenorphine shall be utilized as a base or in the form of a pharmaceutically acceptable salt formed with an inorganic or organic acid, such as hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid and toluenesulfonic acid.

Preferably, buprenorphine is present as the hydrochloride salt.

Advantageously, the concentration of buprenorphine, expressed as free base, shall be comprised between 0.005 and 0.02% w/v, preferably between 0.006 and 0.01% w/v, expressed as free base.

In a particular embodiment, the concentration of buprenorphine hydrochloride is 0.0075% w/v, expressed as free base.

The concentration of the thickening agent shall be comprised between 0.5% and 10%, w/v, preferably between 0.6% and 8.0% w/v. The type and amount of the thickening agent shall be properly selected to achieve an adequate viscosity to retain the formulation as much as possible under the tongue of the patient, to minimize the absorption through the gastrointestinal tract.

At the same time, the viscosity should be not too high to retard the release of the active ingredient from the matrix and hence, its local absorption.

More preferably, the concentration of the thickening agent may be between 1.0 and 6.0% w/v.

In particular embodiments, said concentration is 1.0% w/v, or 1.5% w/v, or 2.0% w/v, or 6.0% w/v.

Advantageously, the thickening agent may be selected from water-soluble polysaccharides such as alginates, carrageenans, pectin, water-soluble derivatives of cellulose: alkylcelluloses hydroxyalkylcelluloses and hydroxyalkylalkylcelluloses, such as methylcellulose, hydroxymethylcellulose, hydroxyethylcellulose, hydroxypropylcellulose, hydroxyethylmethylcellulose, hydroxypropylmethylcellulose, hydroxybutylmethylcellulose, cellulose esters and hydroxyalkylcellulose esters such as cellulose acetate phthalate (CAP), hydroxypropylmethylcellulose (HPMC); carboxyalkylcelluloses, carboxyalkylalkylcelluloses, carboxyalkylcellulose esters such as carboxymethylcellulose and their alkali metal salts; water-soluble synthetic polymers such as polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone (PVP) and polycrotonic acids; also suitable are phthalated gelatin, gelatin succinate, crosslinked gelatin, shellac, water-soluble chemical derivatives of starch, cationically modified acrylates and methacrylates possessing, for example, a tertiary or quaternary amino group, such as the diethylaminoethyl group, which may be quaternized if desired.

Preferably, the thickening agent is a water-soluble cellulose derivative selected from group consisting of hydroxyethylcellulose (HEC) or an alkali metal salt of carboxymethylcellulose (CMC) such as the sodium salt.

In fact, the thickening agents belonging to said classes may provide the suitable viscosity, while with other agents of the class of gums, such as xanthan gum, the viscosity of the formulation turned out to be too high.

Advantageously, the viscosity of the formulation at 25±2° C. shall be comprised between 500 and 2300 mPas (1 mPas corresponds to 1 centipoise), preferably between 700 and 2100 mPas The viscosity may be determined by any known method, for example using a rheometer.

Advantageously, the pH of the formulation of the invention may be comprised between 5.0 and 7.0, more advantageously between 5.2 and 6.8, preferably between 5.5 and 6.5.

When a water soluble cellulose derivative is used, preferred formulations have a pH between 5.5 and 6.5 and an amount of thickening agent comprised between 1.0% and 2.0% w/v, even more preferably of 1.5% w/v. The preferred thickening agent of this class may be hydroxyethylcellulose. Said excipient is commercially available as Natrosol 250 HX™.

Any buffering agent able of providing the pH maybe used, for example phosphate or citrate buffers as sodium or potassium salts. The skilled person in the art shall determine the proper amount.

In a preferred embodiment, anhydrous citric acid and sodium citrate anhydrous is used as buffering agent.

Said formulation may also contain other excipients such as flavoring agents and/or sweeteners.

Flavoring agents may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combinations thereof. A representative list of examples includes mint oils, cocoa, and citrus oils such as lemon, orange, grape, lime and grapefruit and fruit essences including apple, pear, peach, grape, strawberry, raspberry, cherry, plum, pineapple, apricot or other fruit flavors.

Other useful flavorings include aldehydes and esters such as benzaldehyde (cherry, almond), citral i.e., alpha-citral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanol (green fruit), and 2-dodecenal (citrus, mandarin), combinations thereof and the like.

The sweeteners may be chosen from the following non-limiting list: glucose (corn syrup), dextrose, invert sugar, fructose, and combinations thereof; saccharin and its various salts such as the sodium salt; dipeptide sweeteners such as aspartame; dihydrochalcone compounds, glycyrrhizin; *Stevia rebaudiana* (Stevioside); chloro derivatives of sucrose such as sucralose; sugar alcohols such as sorbitol, mannitol, xylitol, and the like. Also contemplated are hydrogenated starch hydrolysates and the synthetic sweetener 3,6-dihydro-6-methyl-1-1-1,2,3-oxathiazin-4-one-2,2-dioxide, particularly the potassium salt (acesulfame-K), and sodium and calcium salts thereof. Other sweeteners may also be used.

Typically, the skilled person in art shall select the sweetener and/or flavoring agent among those considered safe for neonatal administration.

Said formulation may also contain permeation enhancers such as propylene glycol, and polyoxyl hydrogenated castor oil derivatives, for example polyoxyl 40 hydrogenated castor oil (commercially available as Kolliphor RH 40™).

In preferred embodiment, the formulation has the following composition: 0.05-0.01% w/v buprenorphine hydrochloride expressed as a base, 1.5% w/v hydroxyethylcellulose, 0.12% w/v anhydrous citric acid, 1.13% w/v sodium citrate anhydrous, water for injection, and its pH is of 6.0±0.3.

In an alternative embodiment, the formulation may have the following composition: 0.05-0.01% w/v buprenorphine hydrochloride expressed as a base, 6.0% w/v sodium carboxymethylcellulose, 0.12% w/v anhydrous citric acid, 1.13% w/v sodium citrate anhydrous, water for injection, and its pH is of 6.0±0.3.

More details are reported in the International PCT patent application no. PCT/EP2018/078447 and U.S. application Ser. No. 16/164,282, the entire content of each of which is incorporated herein by reference.

The pharmaceutical formulations can be prepared according to known methods.

In a preferred embodiment, the pharmaceutical formulation is sterile and pre-filling is carried out under aseptic conditions is carried out according to methods known in the art.

Even though it less preferred, the pharmaceutical formulation can be in form of a dry powder to be dissolved extemporaneously before use.

Therefore, the invention is also directed to a kit comprising the system herein disclosed together with a pharmaceutical formulation in form of either ready-to-use aqueous solution or powder to be reconstituted in a suitable vehicle, and instructions to administer said pharmaceutical formulation.

The invention claimed is:

1. A system comprising:
a pre-fillable syringe with a syringe barrel and a syringe tip;
a package suitable and intended for receiving the pre-fillable syringe;
a replacement cap (300) for the pre-fillable syringe (100), wherein
the syringe tip is provided with a tip cap,
the replacement cap comprises an inner cap for an engagement with the syringe tip and an outer collar above the inner cap for mounting the replacement cap on the syringe barrel, and
the package is suitable and intended for receiving the replacement cap.

2. The system according to claim 1, wherein
the package comprises a package body forming a first cavity, defined by a sidewall and a bottom wall,
the pre-fillable syringe is arranged in said first cavity,
a plurality of second receiving elements are provided in the first cavity of the package body, in which the syringe barrel is received, and
a distal end of the syringe barrel is supported by a first of the second receiving elements and a proximal end of the syringe barrel is supported by a second of the second receiving elements (7).

3. The system according to claim 2, wherein
the replacement cap is arranged in the package, such that an opening of the replacement cap is oriented along a vertical axis of the package body, and
an opening area of the replacement cap is oriented parallel to the bottom wall of the package body.

4. The system according to claim 2, wherein
at least one third receiving element is provided in the first cavity of the package body, in which a rod of the pre-fillable syringe is received,
a gap between the second of the second receiving elements and the third receiving element is provided, and
a finger flange of the pre-fillable syringe projects through said gap such that the finger flange is sandwiched between the second of the second receiving elements and the third receiving element (8).

5. The system according to claim 1, wherein
the replacement cap comprises a foot portion (303).

6. The system according to claim 2, wherein
a first receiving element is provided in the first cavity of the package body,
the replacement cap is received in the first receiving element, and
a foot portion of the replacement cap is received in the first receiving element.

7. The system according to claim 5, wherein
the foot portion is suitable to provide a stable upright positioning of the pre-fillable syringe with the replacement cap on a support surface,
the foot portion comprises a bearing area, which contacts the support surface,
the bearing area comprises an edge, which surrounds a center axis of the replacement cap at an edge-distance,
the edge-distance is at least twice the radius of the syringe barrel, and
the foot portion has a disc-like shape.

8. The system according to claim 2, wherein
the sidewall of the package body is provided with a flange on its upper end,
the package comprises a closure element, which covers the package body at least in part, and
the closure element is arranged on the flange.

9. The system according to claim 1, wherein the syringe is pre-filled with a ready-to-use pharmaceutical formulation.

10. The system according to claim 9, wherein the pharmaceutical formulation is in a form of a solution or an emulsion and comprises one or more active ingredients suitable for oral, intramuscular, or intravenous administration.

11. The system according to claim 9, wherein the pharmaceutical formulation is an aqueous solution or a hydroalcoholic solution.

12. The system according to claim 9, wherein the pharmaceutical formulation is an aqueous solution or a hydroalcoholic solution for sublingual and/or buccal administration comprising buprenorphine as active ingredient.

13. The system according to claim 1, wherein
the inner cap includes an opening for introduction of the syringe tip into the inner cap, and
the outer collar includes a ring arranged above the opening of the inner cap.

14. The system according to claim 13, wherein
the ring is supported by a plurality of struts placed along the circumference of the ring with an equal radial distance to each other, and
the plurality of struts surround the inner cap radially.

15. The system according to claim 14, wherein the plurality of struts project from the ring radially inward and abut the syringe barrel when the replacement cap is placed on the pre-Tillable syringe.

16. A method of using the system according to claim 1, comprising:
a) retrieving the pre-fillable syringe from the package;
b) removing the tip cap from the syringe tip;
c) placing the syringe tip in the replacement cap, which is arranged in the package; and
d) retrieving the pre-fillable syringe with the replacement cap attached to it from the package.

17. A kit comprising:
the system according to claim 1,
a pharmaceutical formulation in a form of either a ready-to-use aqueous solution or a powder to be reconstituted in a suitable vehicle, and
instructions to administer said pharmaceutical formulation.

* * * * *